United States Patent [19]

Rogerson

[11] Patent Number: 4,828,047

[45] Date of Patent: May 9, 1989

[54] SOIL SAMPLER

[76] Inventor: Charles M. Rogerson, Rte. 1, Box 272, Elizabeth City, N.C. 27909

[21] Appl. No.: 167,893

[22] Filed: Mar. 14, 1988

[51] Int. Cl.⁴ .............................................. G01N 1/08
[52] U.S. Cl. ........................................ 173/24; 175/58; 73/864.31
[58] Field of Search ...................... 173/24, 29; 175/20, 175/58; 73/864.31, 864.41; 248/180; 172/22

[56] References Cited

U.S. PATENT DOCUMENTS

| | | | |
|---|---|---|---|
| 3,331,249 | 7/1967 | Roxrud | 173/24 X |
| 3,464,504 | 9/1969 | Stange | 175/58 X |
| 4,356,734 | 11/1982 | Ivanciscis | 73/864.31 |

Primary Examiner—Frank T. Yost
Assistant Examiner—James L. Wolfe
Attorney, Agent, or Firm—Fred K. Carr

[57] ABSTRACT

This invention relates to a method and apparatus for collecting subsamples of soils to be tested for infestation and nutrient content. The apparatus includes a sampling tube which is mounted on a collecting wheel which is mounted on a frame. During operation, the apparatus is lifted off the ground. To take a sample, the apparatus is lowered such that the wheel makes contact with the ground. This causes the wheel to rotate, forcing the sampling probe into the ground. The sample empties into the interior of the wheel where it mixes. The mixed sample is later removed and boxed for testing.

5 Claims, 4 Drawing Sheets

SOIL SAMPLER

FIELD OF THE INVENTION

This invention relates to a method and apparatus for collecting consecutive topsoil samples to provide a composite sample which is a representative of the soil from a designated sampling area. More particularly, it relates to a method and apparatus for collecting soil samples to be tested for nutrient content and possible insect infestation.

BACKGROUND OF THE INVENTION

It is a common farming practice to collect soil samples from designated areas such that the sample can be analyzed to determine if the soil is infested with insects or lacks particular nutrients needed for best crop production. In practice, a farmer designates an area to be sampled, and thereafter proceeds to collect a composite sample representative of the soil from the area. Most often, the farmer predetermines a pattern for sampling and manually digs samples with a trowel or related tool until a composite sample of desired amount is obtained. This process is slow and laborious requiring a lot of walking and digging.

There have been attempts in the past to design sampling devices which would decrease the amount of labor required in taking soil samples. U.S. Pat. No. 3,625,296 discloses a wheeled device having a clamming digger foot which samples and throws the sample upward and forward into a container. This device has not met the needs, and is not widely used in soil sampling. It can be appreciated that there is a continued need for an effective device to take soil samples. After much research, the presently disclosed soil sampler was designed.

SUMMARY OF THE INVENTION

In summary, the invention relates to an apparatus for collecting soil samples having a sampling tube on a collecting wheel mounted on a support frame. The apparatus is attached to a tractor or other suitable vehicle for traveling in a field. During operation, the apparatus is lifted off the ground. To take a sample, the apparatus is lowered such that the collecting wheel disk makes contact with the ground causing it to rotate. On rotation, the sampling tube is forced into the soil collecting a sample which empties into the interior of the collecting wheel to form a composite sample representative of the designated area. After two or three rotations, the apparatus is lifted off the ground until the next sampling time in accordance with the sampling pattern.

An object of the present invention is to provide an apparatus and method for collecting soil samples.

Another object is to provide an apparatus for collecting soil samples in which subsamples of soil can be collected according to a predetermined pattern to provide a composite sample representative of a designated area.

Another object is to provide an apparatus for collecting soil samples which can be mounted on a vehicle.

Still another object is to provide an apparatus for collecting soil samples which can be mounted on a vehicle and take soil samples while the vehicle is performing another task such as discing.

BRIEF DESCRIPTION OF THE INVENTION

FIG. 1 is a front plain view of the invention.
FIG. 2 is a top plain view of the invention.
FIG. 3 is a view of the invention showing the collecting wheel with sampling tube.
FIG. 4 is a sectional view of the collecting wheel taken at mid-section.

DETAILED DESCRIPTION

Figure 1:
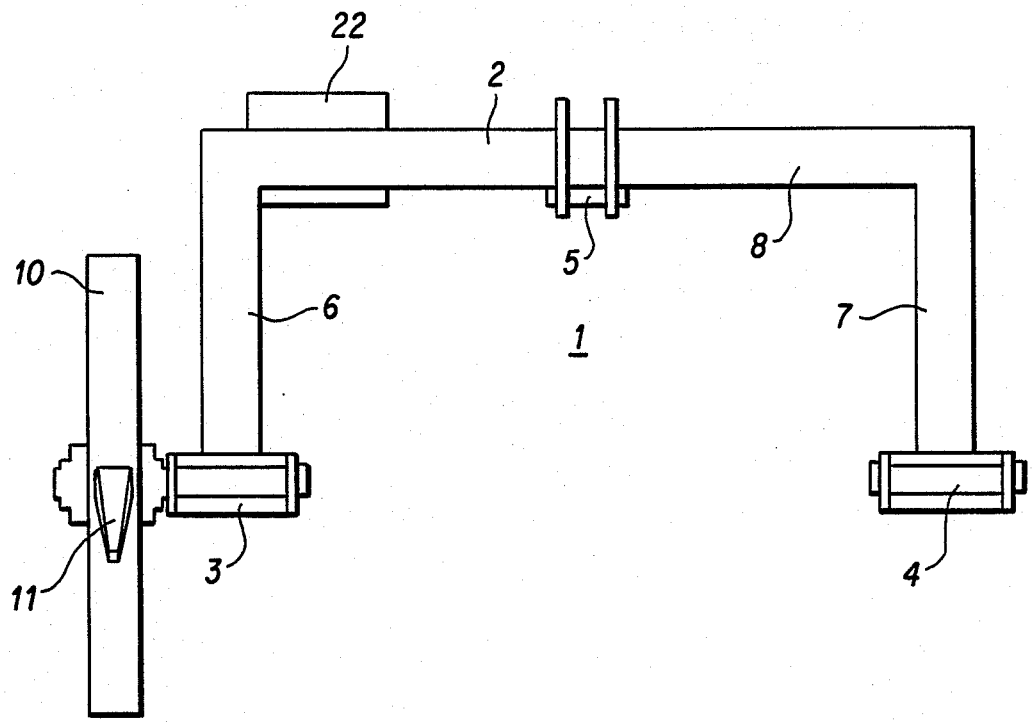

A preferred embodiment of the apparatus is seen in FIG. 1, generally designated (1). It includes an inverted U-shaped support frame (2) for collecting wheel (10) having sampling tube (11). Frame (2) has top member (8) and side members (6) and (7) with side members welded or otherwise secured to the top member. Frame (2) further includes three hitch points for attachment of the frame to the three-point, quick hook up system of a tractor. Attachment point (3) is secured to side member (6), attachment (4) is secured to side member (7), and attachment point (5) is secured to top member (8). The three-point, quick hook-up system is a common hook-up system on tractors. It has a hydraulic system allowing the operator to raise and lower the equipment attached to it. There is a weightrack (22) attached to frame (2) such that dead weights can be placed in it for additional weight.

The soil sampling mechanism includes collecting wheel (10) and sampling tube (11). Wheel (10) has a sleeve bearing attachment to frame (2) allowing the wheel to freely rotate when in contact with the ground. As wheel (10) rotates, sampling tube (11) is forced into the soil collecting a sample of soil. As the tube rotates up with the turn of wheel (10), the sample drops into the interior of wheel (10).

Figure 2:
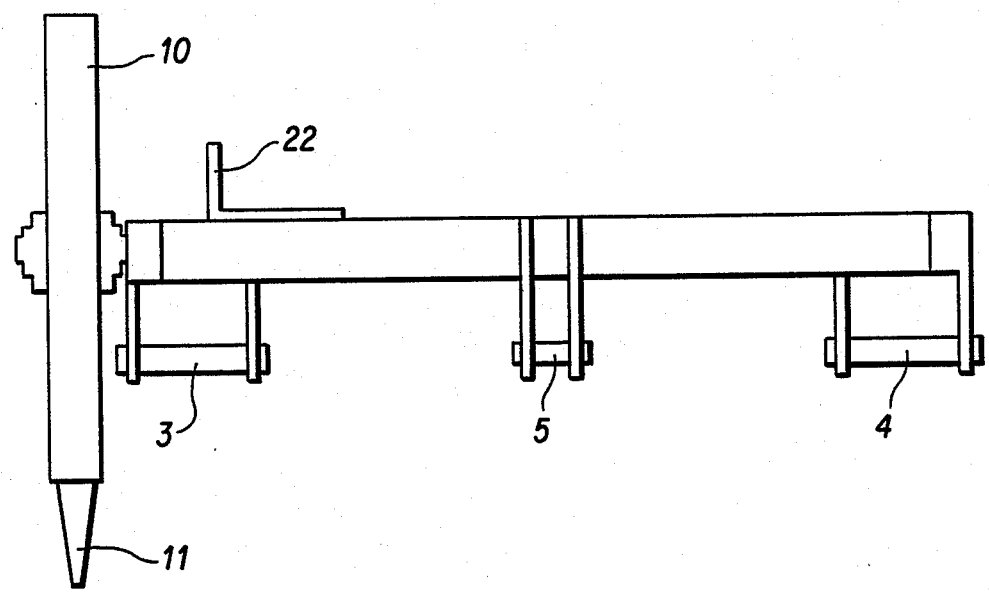

Referring the FIG. 2, there is shown a top view of the sampling apparatus (1). This figure demonstrates how the hitch points (3), (4), and (5) are attached to frame (2). Sampling tube (11) is in a horizontal position in this figure.

Figure 3:
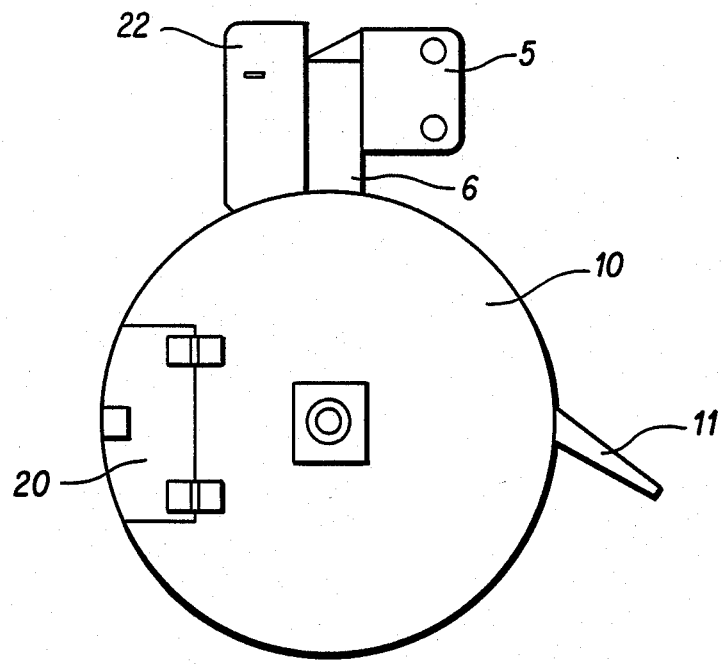

The sampling mechanism is best seen in FIG. 3. Wheel (10) is rotatably connected to frame (2). Sampling tube (11) is attached to wheel (10). In a preferred embodiment, sampling tube (11) is attached at a slight downward angle. Wheel (10) has hinged door (20) for removing the composite sample from interior of wheel (10) after collection. In a preferred embodiment, wheel (10) has a 24 inch diameter, but other sizes are possible.

Figure 4:
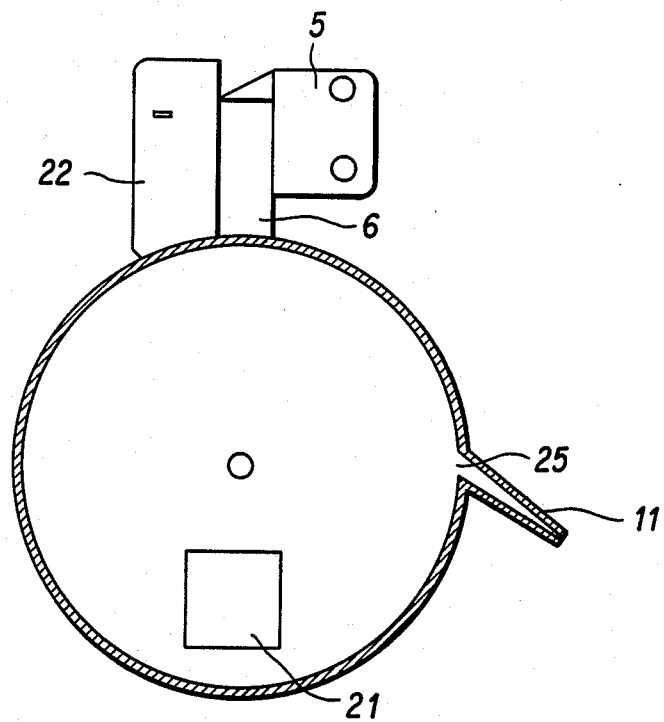

FIG. 4 is a cut-away view of wheel (10) with cut-away being at center line. Weight (21) is attached to interior of wheel (10) to cause the wheel to rest in position where sampling tube (11) is in horizontal position when wheel (10) is not in contact with the ground. This prevents possible damage to tube (11) when wheel (10) is lowered to the ground.

Further reference to FIG. 4 shows an open channel (25) between sampling tube (11) and rim of wheel (10). This allows collected soil to empty into interior of wheel (10) and mix with other samples as the wheel rotates. The sample is removed by opening door (20).

During operation, the sampling apparatus (1) is preferably attached to a tractor by a three-point, quick hitch attachment with hydraulic lift system. The operator predetermines sites to be sampled. When the operators come to a sample site, he lowers the apparatus to the point that wheel (10) makes contact with the ground causing wheel to rotate. As wheel (10) rotates, sampling tube (11) is forced into the soil collecting sample which empties into the interior of wheel (10) when it rotates upward. Typically, the operator allows the wheel to rotate 2-3 times at each sample site collecting 2-3 samples. Within the sampling pattern, there typically are 10-15 sampling sites. It should be pointed out that the tractor can tow other machinery such as a disc when the sampling apparatus is attached allowing the operator to collect samples while performing other field preparation work. Wheel (10) does not support the weight of the apparatus, its function is to rotate forcing sampling tube (11) into the ground when in contact with the ground. The weight of the sampling apparatus (1) is supported by the three-point hookup of the tractor (not shown).

In a preferred embodiment, wheel (10) has the dimensions of twenty four inches in diameter, and a rim width of two and one-half inches. Sampling tube (11) is six inches in length, and is positioned generally downward as in seen in FIG. 3. In other embodiments, other sizes are possible.

Although the apparatus of this invention as described is attached to a tractor with a three-point, quick hook system, it will be obvious to one skilled in the art that a device could easily be constructed to attach the invention to other vehicles such as a jeep or truck. One would need only point of attachment and a hydraulic system for raising and lowering the device.

What is claimed is:

1. An apparatus for collecting samples of topsoil, attachable to a vehicle, comprising:
   a. a frame having means for attachment to a vehicle;
   b. an axle rotatably mounted on said frame;
   c. a collecting wheel secured to said axle to cause said axle to rotate when said wheel is in contact with the ground;
   d. a sampling tube, connected at one end to said wheel and the other end extending generally outward, for collecting topsoil samples when said wheel is in contact with the ground, where the connection of said tube to said wheel has channel allowing the sample to dump into an interior cavity of said wheel;
   e. a door on said wheel for removing collected sampled from interior of wheel; and
   f. a weight attached to interior wall of said wheel, being attached at right angle of said tube, causing said tube to assume horizontal resting position when said wheel is not in contact with ground.

2. An apparatus as recited in claim 1, further comprising:
   a weight rack attached to said frame for placing additional weight when sampling in hard soil.

3. An apparatus as recited in claim 1, wherein:
   said tube is between about 4 to 8 inches in length.

4. An apparatus as recited in claim 3, wherein:
   said tube is between about 1 to 3 inches in width.

5. An apparatus as recited in claim 1, further comprising:
   three hitch points for attachment of said frame to the three-point, quick hook-up system of a tractor.

* * * * *